US00PP26594P3

(12) United States Plant Patent
Trees

(10) Patent No.: US PP26,594 P3
(45) Date of Patent: Apr. 5, 2016

(54) ***MONARDA* PLANT NAMED 'BALBALMAC'**

(50) Latin Name: *Monarda didyma*
Varietal Denomination: Balbalmac

(71) Applicant: Ball Horticultural Company, West Chicago, IL (US)

(72) Inventor: Scott Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 102 days.

(21) Appl. No.: 14/121,139

(22) Filed: Aug. 5, 2014

(65) Prior Publication Data

US 2016/0044853 P1 Feb. 11, 2016

(51) Int. Cl.
*A01H 5/00* (2006.01)

(52) U.S. Cl.
USPC ..... Plt./455

(58) Field of Classification Search
USPC ..... Plt./455
See application file for complete search history.

*Primary Examiner* — Annette Para
(74) *Attorney, Agent, or Firm* — Audrey Charles

(57) ABSTRACT

A new and distinct cultivar of *Monarda* plant named 'Balbalmac', characterized by its deep lilac-colored inflorescences, dark green-colored foliage, good powdery mildew resistance, and moderately vigorous, upright-compact growth habit, is disclosed.

1 Drawing Sheet

Latin name of genus and species of plant claimed: *Monarda didyma.*

Variety denomination: 'Balbalmac'.

BACKGROUND OF THE INVENTION

The present invention relates to a new and distinct cultivar of *Monarda* plant botanically known as *Monarda didyma* and hereinafter referred to by the cultivar name 'Balbalmac'.

The new cultivar originated in a controlled breeding program in Guadalupe, Calif. The objective of the breeding program was the development of *Monarda* cultivars that are early flowering, have good powdery mildew resistance, and a compact growth habit.

The new *Monarda* cultivar is an irradiation-induced sport of Balmy Purple 'Balbalmurp', U.S. Plant Pat. No. 22,561, characterized by its dark purple-colored inflorescences, dark green-colored foliage having good powdery mildew resistance, and moderately vigorous, upright-compact growth habit. The irradiation occurred on May 2011. The new cultivar was discovered as a side shoot and selected during September 2012 in a controlled environment in Guadalupe, Calif.

Asexual reproduction of the new cultivar by terminal stem cuttings since September 2012 in Guadalupe, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balbalmac' as a new and distinct cultivar of *Monarda* plant:

1. Deep lilac-colored inflorescences;
2. Dark green-colored foliage;
3. Good powdery mildew resistance; and
4. Moderately vigorous, upright-compact growth habit.

Of the many commercially available *Monarda* cultivars, the most similar in comparison to the new cultivar is the parent Balmy Purple 'Balbalmurp', U.S. Plant Pat. No. 22,561. However, in side by side comparisons, plants of the new cultivar differ from plants of 'Balbalmurp' in at least the following characteristics:

1. Plants of the new cultivar have an inflorescence color different from plants of 'Balbalmurp'; and
2. Plants of the new cultivar have lighter colored stigmas than plants of 'Balbalmurp'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balbalmac'. The plants were grown in 1.5 gallon containers for approximately two months in a greenhouse and 11 weeks outdoors in West Chicago, Ill. Plants were given two pinches prior to transplant.

DETAILED BOTANICAL DESCRIPTION

Figure 1:
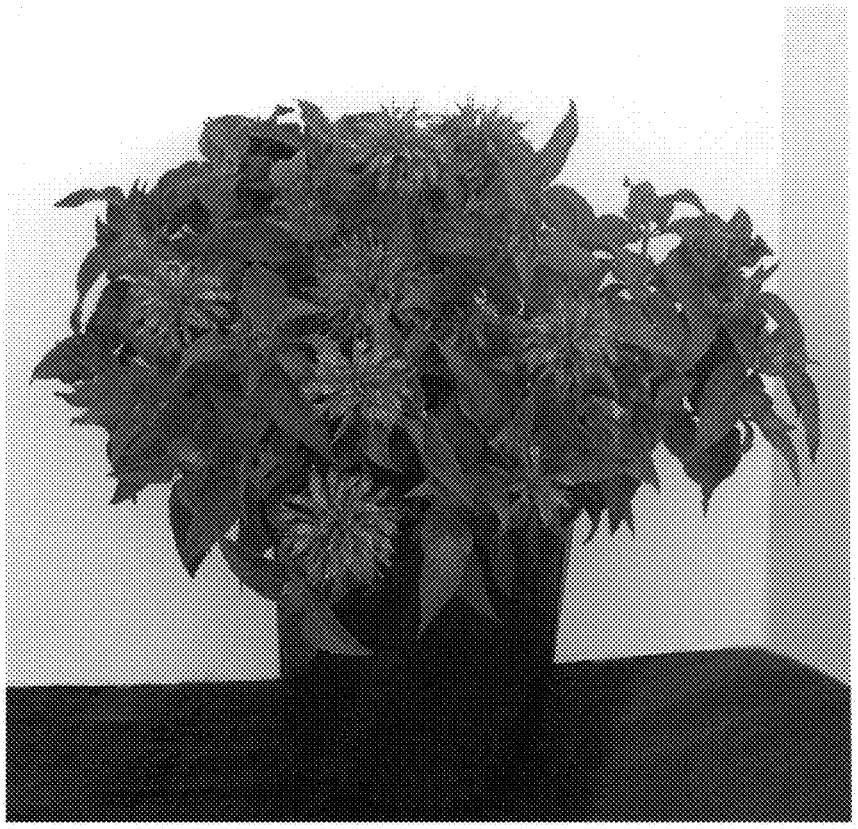
FIG. 1 illustrates a side view of the overall growth and flowering habit of 'Balbalmac'.
Figure 2:
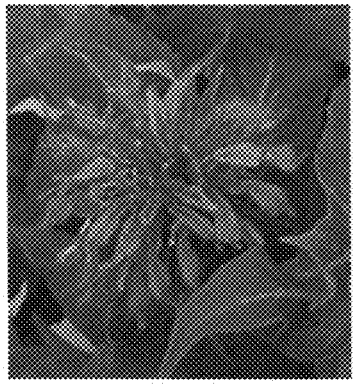
FIG. 2 illustrates a close-up view of an individual inflorescence of 'Balbalmac'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2014 under natural light conditions in West Chicago, Ill.

The following descriptions and measurements describe plants produced from cuttings from stock plants and grown under conditions comparable to those used in commercial practice. The plants were grown utilizing a soilless growth medium in one-gallon containers for approximately two months in a greenhouse and two months outdoors in Elburn, Ill. Plants were given one pinch prior to transplant and one pinch two weeks after transplant. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Monarda didyma* cultivar Balbalmac.

Parentage:

*Parent*.—Balmy Purple 'Balbalmurp', U.S. Plant Pat. No. 22,561.

Propagation:

*Type cutting*.—Terminal stem.

*Time to initiate roots*.—Approximately 7 to 10 days.

*Time to produce a rooted cutting*.—Approximately 28 to 35 days.

*Root description*.—Fine, fibrous white to brown in color.

*Rooting habit*.—Freely branching.

Plant description:

*Commercial crop time*.—Approximately 12 to 14 weeks from a rooted cutting to finish in a 15 cm pot.

*Growth habit and general appearance*.—Moderately vigorous, upright-compact.

*Size*.—Height from soil level to top of plant plane: Approximately 26.0 cm. Width: Approximately 32.5 cm.

*Branching habit*.—Freely branching. Pinching enhances lateral branching. Quantity of main branches per plant: Approximately 4.

*Branch*.—Shape: Square in cross section. Strength: Strong. Length to base of inflorescence: Approximately 22.0 cm. Diameter: Approximately 5.0 mm. Length of central internode: Approximately 2.3 cm. Texture: Densely pubescent on edges. Color of young stems: 146C. Color of mature stems: 146B, becoming woody 200B with age.

Foliage description:

*General description*.—Quantity of leaves per branch: Approximately 10. Fragrance: Strong, sage-like. Form: Simple. Arrangement: Opposite.

*Leaves*.—Aspect: Perpendicular to obtuse angle to stem. Shape: Ovate to Lanceolate. Margin: Serrate. Apex: Acute. Base: Rounded. Venation pattern: Pinnate. Length of mature leaf: Approximately 6.5 cm. Width of mature leaf: Approximately 3.1 cm. Texture of upper and lower surfaces: Slightly rugose, densely pubescent. Color of upper surface of young and mature foliage: Closest to N137A with venation of 146C. Color of lower surface of young and mature foliage: Closest to 137B with venation of 146D.

*Petiole*.—Length: Approximately 8.0 mm. Diameter: Approximately 2.0 mm. Texture: Densely pubescent. Color: 146B.

Flowering description:

*Flowering habit*.—'Balbalmac' is freely flowering under outdoor growing conditions blooming from late spring through summer.

*Lastingness of individual flower*.—Approximately 5 to 7 days.

Inflorescence description:

*General description*.—Type: Dense terminal verticillasters, not persistent, facing upward and outward. Quantity of inflorescences per plant: Approximately 18. Fragrance: Strong, sage-like. Depth or height of inflorescence: Approximately 4.0 cm. Width of inflorescence: Approximately 5.5 cm, expands to approximately 7.0 cm as innermost flowers senesce. Quantity of fully-open flowers per inflorescence: Approximately 40.

*Peduncle*.—Shape: Square in cross section. Strength: Strong. Aspect: Erect. Length: Approximately 1.0 cm. Diameter: Approximately 4.0 mm. Texture: Densely pubescent on edges. Color: 146B.

Flower description:

*Type*.—Single, bilabiate.

*Bud*.—Rate of opening: Generally takes 2 to 3 days for bud to progress from first color to fully open flower.

*Bud just before opening*.—Shape: Tubular, upper portion strongly recurved. Length: Approximately 1.9 cm. Diameter: Approximately 1.5 mm. Texture: Densely pubescent. Color: N81 A.

*Corolla*.—Shape: Two lips, upper lip hooded; lower lip, a single lobe; lips fused. Depth (height): Approximately 3.9 cm. Width: Approximately 6.0 mm. Length: Approximately 1.8 cm.

*Upper lip*.—Shape: Linear, hooded. Aspect: Erect. Margin: Entire. Apex: Two acute tips. Length: Approximately 1.3 cm. Width: Approximately 1.0 mm. Texture of inner surface: Glabrous. Texture of outer surface: Densely pubescent. Color of inner surface when first and fully open: N80B. Color of outer surface when first and fully open: N80A.

*Lower lip*.—Shape: Oblanceolate. Margin: Entire. Apex: Notched lobe at apex about 4.0 mm in length and 1.0 mm in width. Length: Approximately 1.7 cm. Width: Approximately 6.0 mm. Texture of upper surface: Glabrous. Texture of lower surface: Densely pubescent. Color of upper surface when first and fully open: N80A. Color of lower surface when first and fully open: Between N80A and N80B.

*Corolla tube*.—Length: Approximately 1.9 cm. Width: Approximately 2.0 mm. Texture of inner surface: Glabrous. Texture of outer surface: Densely pubescent. Color: N80A.

*Calyx*.—Shape: Tubular. Length: Approximately 9.0 mm. Diameter: Approximately 2.0 mm.

*Sepals*.—Quantity per flower: 5, fused except for acuminate apex of 1.0 mm in length having an entire margin. Length: Approximately 9.0 mm. Width: Less than 1.0 mm. Texture of inner surface: Sparsely pubescent. Texture of outer surface: Densely pubescent. Color of inner surface: 145B with tips of 187A. Color of outer surface: 145A with tips of 187A.

*Bracts*.—Quantity: Approximately 25 per inflorescence in multiple whorls. Shape: Ovate to narrowly ovate. Length of larger: Approximately 4.5 cm. Width of larger: Approximately 2.0 cm. Length of smaller: Approximately 1.0 cm. Width of smaller: Less than 1.0 mm. Texture of upper and lower surfaces: Densely pubescent. Color of upper surface of larger bracts: Closest to 139A with center of base of 139D. Color of lower surface of larger bracts: 137B. Color of upper and lower surfaces of smaller bracts: 139D with tips of 187A.

*Reproductive organs*.—Androecium: Stamen quantity: 2 per flower, dorsifixed. Filament length: Approximately 3.7 cm. Filament length of fixed portion: Approximately 1.5 cm. Filament color: NN155D, opaque with an overlay of N81B near anther. Anther shape: Narrowly elliptic to oblong. Anther length: Approximately 2.0 mm. Anther color: 83C. Pollen amount: Moderate. Pollen color: NN155D. Gynoecium: Pistil quantity: 1 per flower. Pistil length: Approximately 3.9 cm. Stigma shape: Cleft, two-parted. Stigma length: Approximately 2.0 mm. Stigma color: 90A. Style length: Approximately 3.6 cm. Style color: NN155D, opaque with an overlay of 90A near stigma. Ovary length: Approximately 1.0 mm. Ovary color: 158B.

Seed and fruit production: Neither seed nor fruit production has been observed.

Disease and pest resistance: Resistance to pathogens and pests common to *Monarda* has not been observed.

What is claimed is:

1. A new and distinct cultivar of *Monarda* plant named 'Balbalmac', substantially as herein shown and described.

* * * * *